United States Patent
Schaede

(10) Patent No.: US 7,659,984 B2
(45) Date of Patent: Feb. 9, 2010

(54) DEVICE FOR CONTROLLING MATERIAL

(75) Inventor: Johannes Georg Schaede, Würzburg (DE)

(73) Assignee: KBA-Giori S.A., Lausanne (CH)

( * ) Notice: Subject to any disclaimer, the term of this patent is extended or adjusted under 35 U.S.C. 154(b) by 0 days.

(21) Appl. No.: 11/787,978

(22) Filed: Apr. 18, 2007

(65) Prior Publication Data

US 2007/0285664 A1 Dec. 13, 2007

(51) Int. Cl.
*G01N 21/84* (2006.01)
(52) U.S. Cl. ..................................... 356/429
(58) Field of Classification Search .......... 356/429–431
See application file for complete search history.

(56) References Cited

U.S. PATENT DOCUMENTS

| | | | |
|---|---|---|---|
| 3,317,738 A | | 5/1967 | Piepenbrink et al. |
| 3,574,263 A | * | 4/1971 | Del Elia ..................... 434/355 |
| 4,233,663 A | * | 11/1980 | Sugawara et al. ........... 358/296 |
| 4,254,643 A | | 3/1981 | Mitter |
| 4,259,591 A | | 3/1981 | Morris et al. |
| 4,407,197 A | | 10/1983 | Jeschke |
| 4,647,182 A | | 3/1987 | Pierce |
| 5,548,408 A | * | 8/1996 | Koren ......................... 358/300 |
| 5,565,962 A | * | 10/1996 | Yoshimoto ................... 399/366 |
| 6,081,352 A | * | 6/2000 | Poulsen et al. .............. 358/493 |
| 6,091,834 A | * | 7/2000 | Bradburn ..................... 382/108 |
| 6,192,140 B1 | * | 2/2001 | Reinhard et al. ............. 382/112 |
| 6,307,972 B1 | * | 10/2001 | Riley et al. ................. 358/3.06 |
| 2005/0223922 A1 | | 10/2005 | Giori et al. |

FOREIGN PATENT DOCUMENTS

| | | |
|---|---|---|
| CH | 466 330 A | 6/1969 |
| DE | 433 1965 A | 3/1995 |
| JP | 2-138669 A | 5/1990 |
| JP | 11-190697 | 7/1999 |
| JP | 11-211666 | 8/1999 |
| JP | 2002-372500 | 12/2002 |
| WO | WO 97/10670 | 3/1997 |
| WO | WO 97/48556 | 12/1997 |
| WO | WO 01/85457 A1 | 11/2001 |

* cited by examiner

*Primary Examiner*—Michael P Stafira
(74) *Attorney, Agent, or Firm*—Clifford W. Browning; Krieg DeVault LLP

(57) ABSTRACT

The invention relates to a device for controlling material comprising a sensor device and a lighting device, whereby the material which is to be controlled is guided on a transparent drum.

8 Claims, 3 Drawing Sheets

DEVICE FOR CONTROLLING MATERIAL

Figure 1:
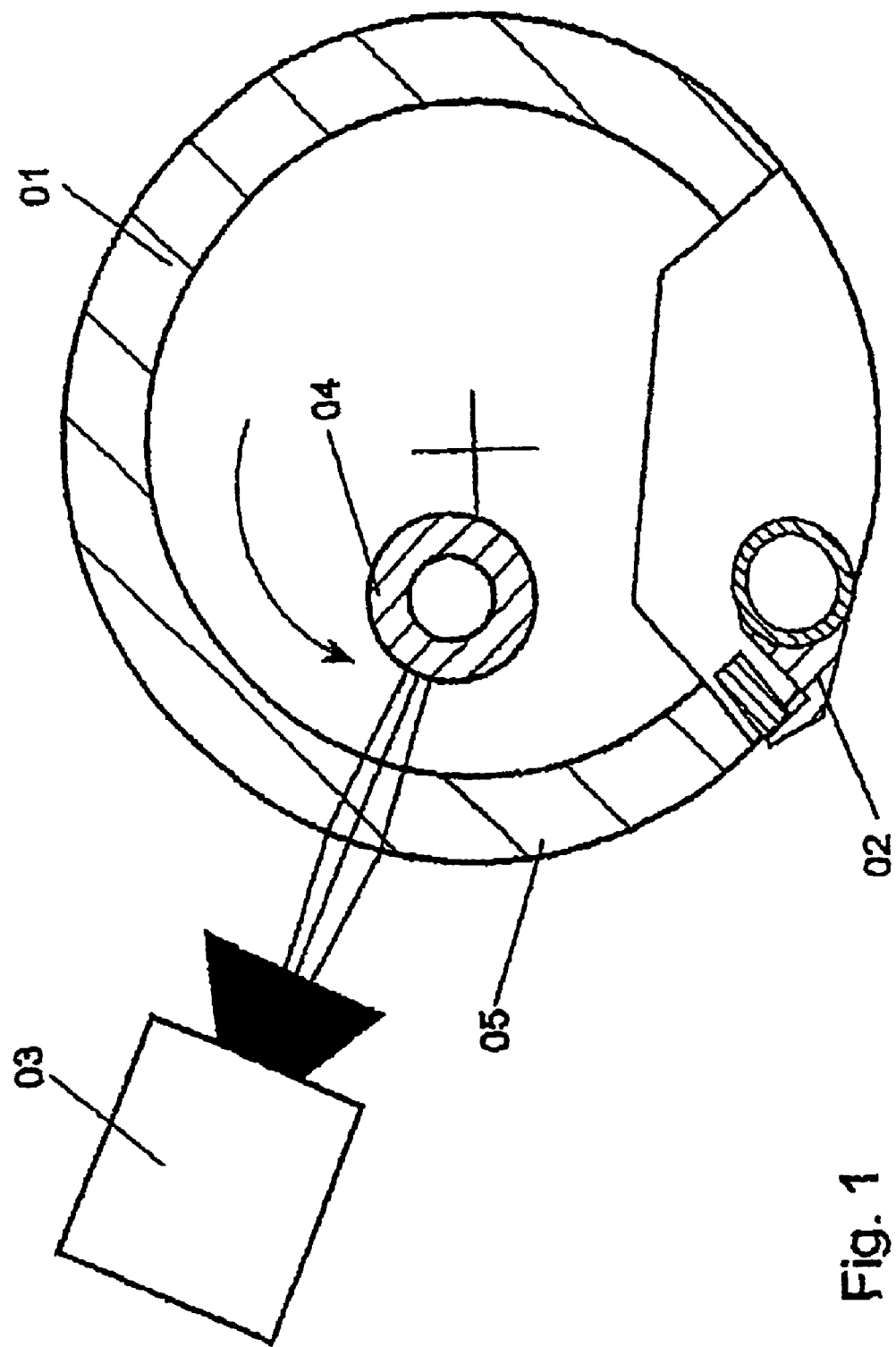

The invention relates to a device to control material according to the preamble of claim 1.

Such devices are known from DE 29 44 322 A1 and U.S. Pat. No. 3,028,502 A.

With the device described in U.S. Pat. No. 3,028,502 A, the material to be controlled is stretched on a transparent drum and can be passed by a sensor unit by means of a corresponding drum rotation. The sensor is installed inside the drum and can be moved via a mobile runner in the direction of the longitudinal axis of the drum. Outside the drum, a lighting unit, that can be moved synchronous to the movement of the sensor unit, is arranged opposite the sensor unit. Through operation of the lighting unit, the printed image printed on the material can be illuminated, whereby, due to the transparent properties of the drum, the sensor unit inside the drum receives an input signal that changes in accordance with the printed image.

With the device described in DE 29 44 322 A, light-optical sensors are arranged within a transparent hollow drum. Outside the drum, there are light sources arranged opposite the light sensors, or a light source arranged over the entire length of the drum. Through illumination of the printed material stretched on the drum, depending on the printed color density, differing light intensities are detected by the sensors.

WO 01 85 586 A1 discloses a device to transport sheet material, in particular securities. So that the light from a light source can pass from outside the drum, with illumination of the printed material, to a sensor unit within the drum, the non-transparent drum has suitably-arranged openings so that, as an overall result, the entire surface area cannot be controlled.

DE 43 31 965 A1 shows a device to inspect X-ray images whereby the light source lies within a transparent drum.

The aim of the invention is to provide a device to control material.

This task is solved through the features of claim 1.

One advantage of the invention in particular is that the sensor unit placed outside the transparent drum is exposed to far less temperature load. Due to the position of the sensor unit outside the drum, it is possible to easily provide adequate cooling of the sensor.

One exemplifying embodiment of the invention is shown in the drawings and will be described below in greater detail.

Figure 2:
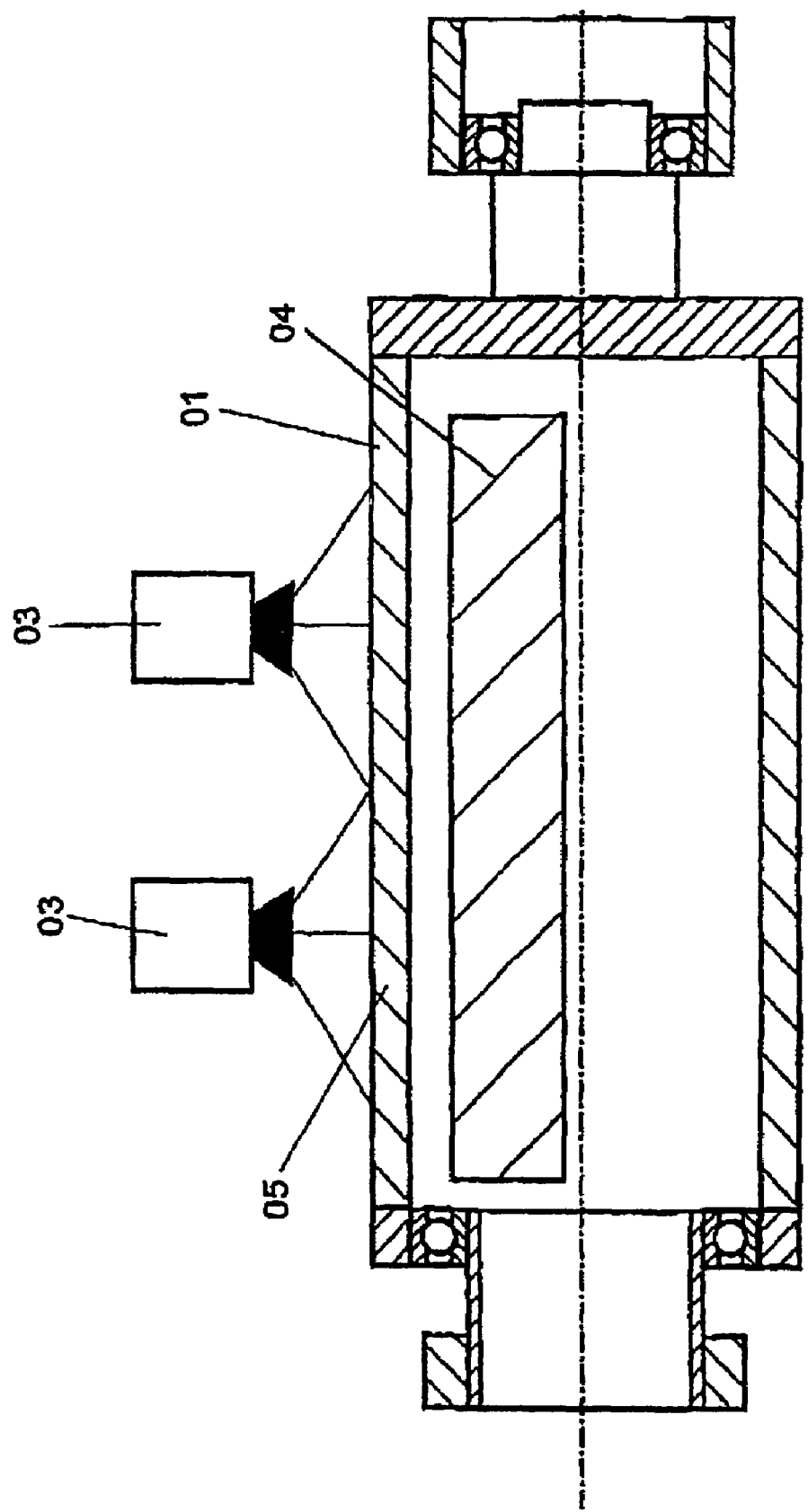
Figure 3:
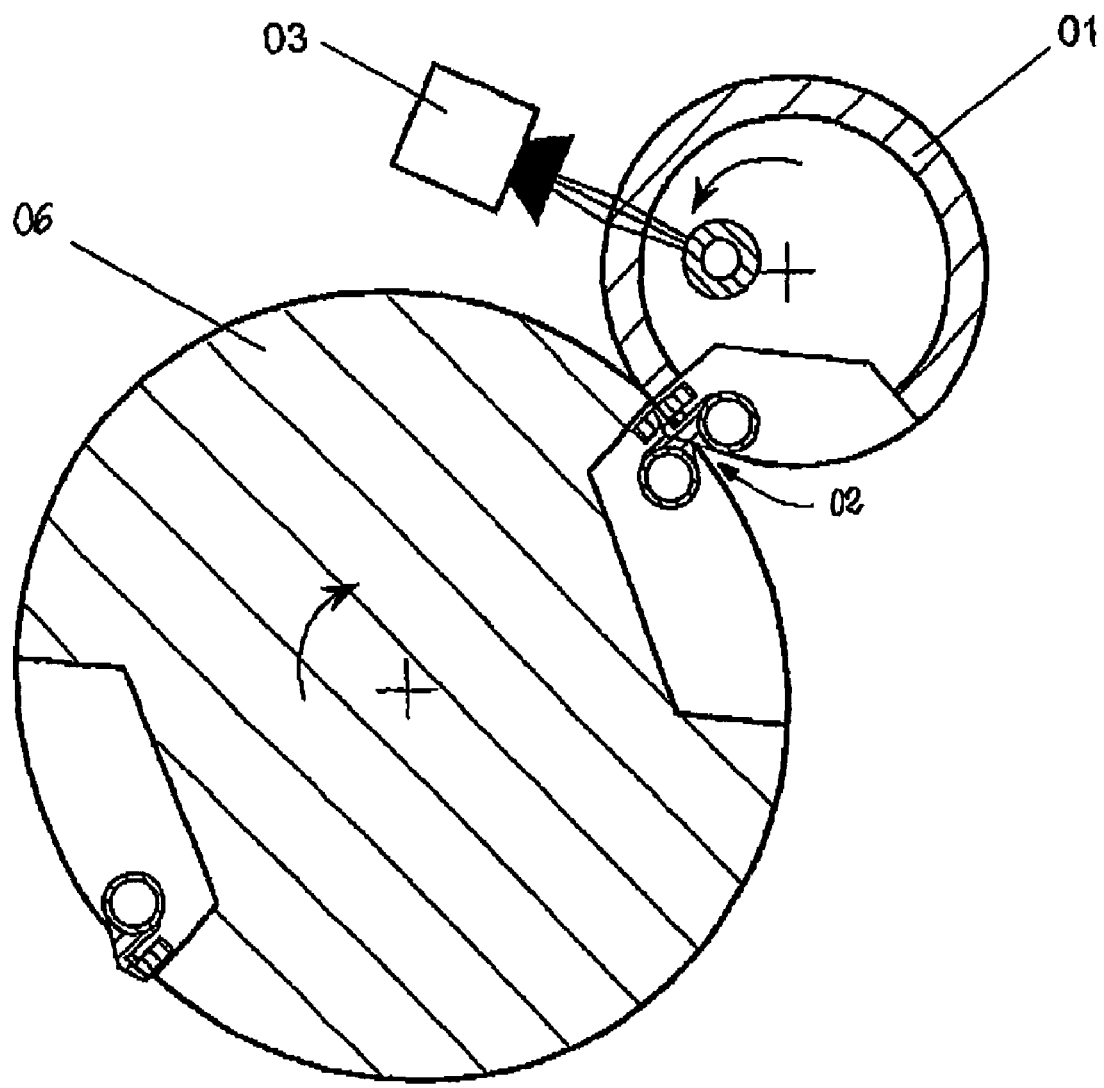

The following is shown:

FIG. 1 a device in cross-section;

FIG. 2 the device according to FIG. 1 in longitudinal section;

FIG. 3 the device according to FIG. 1 with the arrangement of a counter-pressure cylinder in a printing machine.

The device shown in FIG. 1 essentially consists of a transparent drum 01 with a retaining device 02, e.g. a gripper 02 and a sensor unit 03, e.g. a CCD camera 03, arranged outside the drum 01 and opposite a lighting unit 04 arranged inside the drum 01.

To control a material 05, especially a sheet printed with securities, the material 05 is fixed to the gripper 02 so that it can be moved along by rotational drive of the drum 01. Here the material 05 surrounds the drum 01 and nearly its entire surface lies on the transparent drum 01.

Through switching on the lighting device 04, the transparent drum 01 and the adjacent material 05 are illuminated and passed through by light beams, that then enter the lens of the sensor 03. Depending on the printed image on the material 05, the input signal detected by the sensor unit 03 changes such that, by means of a suitable evaluation unit, the printed image on the material 05 can be controlled through evaluation of the output signals from the sensor unit 03.

FIG. 2 shows the device with the drum 01, the sensor unit 03, the lighting unit 04 and the material to be controlled 05 in longitudinal section. It can be seen that the drum 01 is closed on the one front side and open on the other, so that adequate mechanical stability is ensured for the drum 01, and moreover the lighting unit 04 can readily be introduced within the drum 01 and fixed. Through the arrangement of the sensor unit 03 outside the drum 01, the sensors 03, shown in this example as two CCD cameras 09 arranged side by side, are easy to cool.

The lighting unit 04, constituted for example as a type of lighting tube 04, extends substantially over the entire length of the drum 01, so that the material 05 on the drum 01 can be illuminated in all areas. The lenses of the CCD cameras 03 are designed such that each covers half the length of the drum 01.

FIG. 3 schematically shows the device with the drum 01 and the sensor 03 arranged on a counter-pressure cylinder 06 in a securities-printing machine. By means of corresponding arrangement of the grippers 02 on the drum 01 and the counter-pressure cylinder 06, the securities printed in the printing machine can be continuously transferred from the counter-pressure cylinder 06 to the drum 01 and controlled there by the sensor 03.

REFERENCE LIST

01 Drum, transparent
02 Holding device, gripper
03 Sensor unit, CCD camera
04 Lighting unit, lighting tube
05 Material, to be controlled
06 Counter-pressure cylinder

The invention claimed is:

1. Device for controlling a sheet printed with securities, comprising a sensor unit, a lighting unit and an evaluation unit, wherein the sheet to be controlled is led on a transparent rotating drum, wherein the lighting unit is arranged on one side of the rotating drum and the sensor unit on the other side of the rotating drum, wherein the lighting unit extends substantially over the entire length of the rotating drum so that the sheet lying on the rotating drum is illuminated in all areas, wherein the lighting unit and the sensor unit are arranged in a fixed manner with respect to the rotating drum, wherein the sensor unit receives for all areas of the printed sheet an input signal, and wherein, depending on the printed image on the sheet, the input signal detected by the sensor unit changes such that, by means of the evaluation unit, the printed image on the sheet can be controlled through evaluation of the output signals from the sensor unit.

2. Device according to claim 1, wherein the lighting unit is arranged within the periphery of the rotating drum and the corresponding sensor unit is arranged outside the periphery of the rotating drum.

3. Device according to claim 1, wherein the sheet is lying substantially over its entire surface upon the transparent rotating drum.

4. Device according to claim 1, wherein the rotating drum is arranged in a printing machine.

5. Device according to claim 1, wherein the sensor unit is a CCD camera.

6. Device according to claim 1, wherein the sensor unit is cooled.

7. Device according to claim 1, wherein the rotating drum is open at one front end and closed at the other.

8. Device according to claim 1, wherein the lighting unit comprises a lighting tube.

* * * * *

UNITED STATES PATENT AND TRADEMARK OFFICE
CERTIFICATE OF CORRECTION

PATENT NO.         : 7,659,984 B2                                                  Page 1 of 1
APPLICATION NO.    : 11/787978
DATED              : February 9, 2010
INVENTOR(S)        : Johannes Georg Schaede It is certified that error appears in the above-identified patent and that said Letters Patent is hereby corrected as shown below:

On the Title page of the patent, please add

--Related U.S. Application Data (63) Continuation of application No. 10/499,507, filed on Jul. 12, 2004, now Pat. No. 7,215,427, filed as 371 of International Application No. PCT/DE02/04609, filed on Dec. 17, 2002.--

Signed and Sealed this

Twentieth Day of April, 2010

David J. Kappos
*Director of the United States Patent and Trademark Office*